United States Patent [19]

Schloss et al.

[11] Patent Number: 5,733,312

[45] Date of Patent: Mar. 31, 1998

[54] SYSTEM AND METHOD FOR MODULATING THE OUTPUT OF AN IMPLANTABLE MEDICAL DEVICE IN RESPONSE TO CIRCADIAN VARIATIONS

[75] Inventors: Harold C. Schloss, Los Angeles; Gene A. Bornzin, Simi Valley, both of Calif.

[73] Assignee: Pacesetter, Inc., Sylmar, Calif.

[21] Appl. No.: 783,936

[22] Filed: Jan. 17, 1997

[51] Int. Cl.$^6$ .................................................. A61N 1/365
[52] U.S. Cl. ............................................................ 607/17
[58] Field of Search ................................... 607/17, 18, 19, 607/20, 21, 59, 2, 22, 23, 30

[56] References Cited

U.S. PATENT DOCUMENTS

| | | | |
|---|---|---|---|
| 4,365,633 | 12/1982 | Loughman et al. | 607/30 |
| 4,922,930 | 5/1990 | Adkins et al. | 607/19 |
| 4,945,909 | 8/1990 | Fearnot et al. | 607/14 |
| 5,040,534 | 8/1991 | Mann et al. | 607/19 |
| 5,300,092 | 4/1994 | Schaldach | 607/18 |
| 5,476,483 | 12/1995 | Bornzin et al. | 607/17 |

OTHER PUBLICATIONS

Morris–Thurgood, Jayne, et al., "A Rate Responsive Pacemaker That Physiologically Reduces Pacing Rates at Rest," *PACE*, vol. 17, Part II, pp. 1928–1932 (Nov. 1994).

Bornzin, Gene A., et al., "Adjusting Heart Rate During Sleep Using Activity Variance", *PACE*, vol. 17, Part II, pp. 1933–1938, (Nov. 1994).

Chew, Paul H., et al., "Overnight Heart Rate and Cardiac Function in Patients with Dual Chamber Pacemakers", *PACE*, vol. 19, pp. 822–828, (May 1996).

*Primary Examiner*—William E. Kamm
*Assistant Examiner*—Kennedy J. Schaetzle

[57] ABSTRACT

An implantable cardiac pacemaker is provided for delivering pacing pulses to a patient, where the pacing pulses are defined by at least two parameters. The pacemaker allows for transitioning of the two parameters from first values to second values in response to the patient's circadian rhythms, such as in response to the beginning and ending of a sleep cycle. Also provided is an implantable pacemaker for delivering pacing pulses to a patient where the pacing pulses are defined by at least one parameter. The pacemaker allows for selective transitioning of the parameter from a first value to a second value in response to the patient's circadian rhythms.

49 Claims, 2 Drawing Sheets

SYSTEM AND METHOD FOR MODULATING THE OUTPUT OF AN IMPLANTABLE MEDICAL DEVICE IN RESPONSE TO CIRCADIAN VARIATIONS

FIELD OF THE INVENTION

This invention relates to implantable cardiac pacemakers which are rate-responsive. More particularly, this invention relates to implantable cardiac pacemakers which modulate their rate of pacing pulses in response to a patient's circadian rhythms.

BACKGROUND OF THE INVENTION

The intrinsic cardiac rhythmicity of both normal and diseased hearts is subject to circadian variations. For example, minimum heart rate decreases during sleep (Djordjevic, M. et al., "Circadian Variations of Heart Rate and STIM-T Interval: Adaptation for Nighttime Pacing," *PACE* (1989: 12; 1757–1762).

A number of cardiac pacemakers have been developed to sense stages in a patient's circadian rhythm or activity level and to alter the output of pacing pulses in response. For example, U.S. Pat. Nos. 4,922,930 and 5,143,065, both to Adkins et al., disclose a cardiac pacemaker which can vary the rate of pacing pulses in accordance with a wake-sleep cycle based on a model having multiple periods. Each period has a specific duration and utilizes a predicted minimum physiologic need for the patient.

Similarly, U.S. Pat. No. 4,945,909 to Fearnot et al. discloses a pacemaker that paces at a rate defined within a range having variable upper and lower rate limits. These limits change in response to patient activity sensed by the pacemaker. U.S. Pat. No. 5,300,092 to Schaldach also discloses a cardiac pacemaker which can vary the rate of pacing pulses in response to the patient's sensed activity. U.S. Pat. No. 5,476,483 to Bornzin et al. discloses a cardiac pacemaker that varies a base pacing rate of a predetermined transfer function according to sensed activity levels.

These pacemakers can produce a cardiac rhythm that more closely mimics a natural rhythm than pacemakers that do not change their output in response to activity levels or to stages in a patient's circadian rhythm. However, these pacemakers do not fully mimic the changes that naturally occur as a result of a patient's circadian rhythm.

Some patients would benefit from a pacemaker which could vary its output to mimic a natural rhythm more closely. Additionally, as a patient's heart or lifestyle changes over time, it would be advantageous to have a pacemaker which can vary its output in response to a patient's circadian rhythm in a manner that is selectable according to the patient's needs.

SUMMARY OF THE INVENTION

The present invention is an implantable cardiac pacemaker which alters its delivery of pacing pulses in response to the onset of sleep or waking by the patient. In one embodiment, the pacemaker transitions at least two parameters which define the pacing pulses from one set of values to another set of values in response to the onset of sleep or waking. In another embodiment, the pacemaker transitions at least one parameter which defines the pacing pulses from one value to another value by a selectable transfer curve in response to the onset of sleep or waking. The pacemaker comprises a circadian rhythm detector, a processor and output circuitry. The pacemaker can additionally comprise telemetry means. The circadian rhythm detector senses the onset of a stage in the patient's circadian rhythm, such as the onset of a period of sleep or waking. The processor transitions the value of at least one parameter which defines the pacing pulses to another value by a transition curve in response to the onset. The output circuitry alters the pacing pulses sent to the patient due to the value changes. When present, the telemetry means instructs the processor to change the transition curve from a first curve to a second curve.

The present invention advantageously allows for alteration of the pacing pulses in a manner that more closely mimics the natural changes that occur due to the patient's circadian rhythms. The present invention also allows the output of the pacemaker to vary in response to a patient's circadian rhythm in a manner that is selectable according to the patient's needs over time.

DESCRIPTION OF THE DRAWINGS

These features, aspects and advantages of the present invention will become better understood with regard to the following description, appended claims and accompanying figures where:

DETAILED DESCRIPTION OF THE PREFERRED EMBODIMENT

In one embodiment, the present invention is an implantable pacemaker for delivering pacing pulses to a patient where the pacing pulses are defined by at least two parameters. The pacemaker allows for transitioning of the two parameters from first values to second values in response to the patient's circadian rhythms, such as in response to the beginning and ending of a sleep cycle. In another embodiment, the present invention is an implantable pacemaker for delivering pacing pulses to a patient where the pacing pulses are defined by at least one parameter. The pacemaker allows for selective transitioning of the parameter from a first value to a second value in response to the patient's circadian rhythms.

Figure 1:
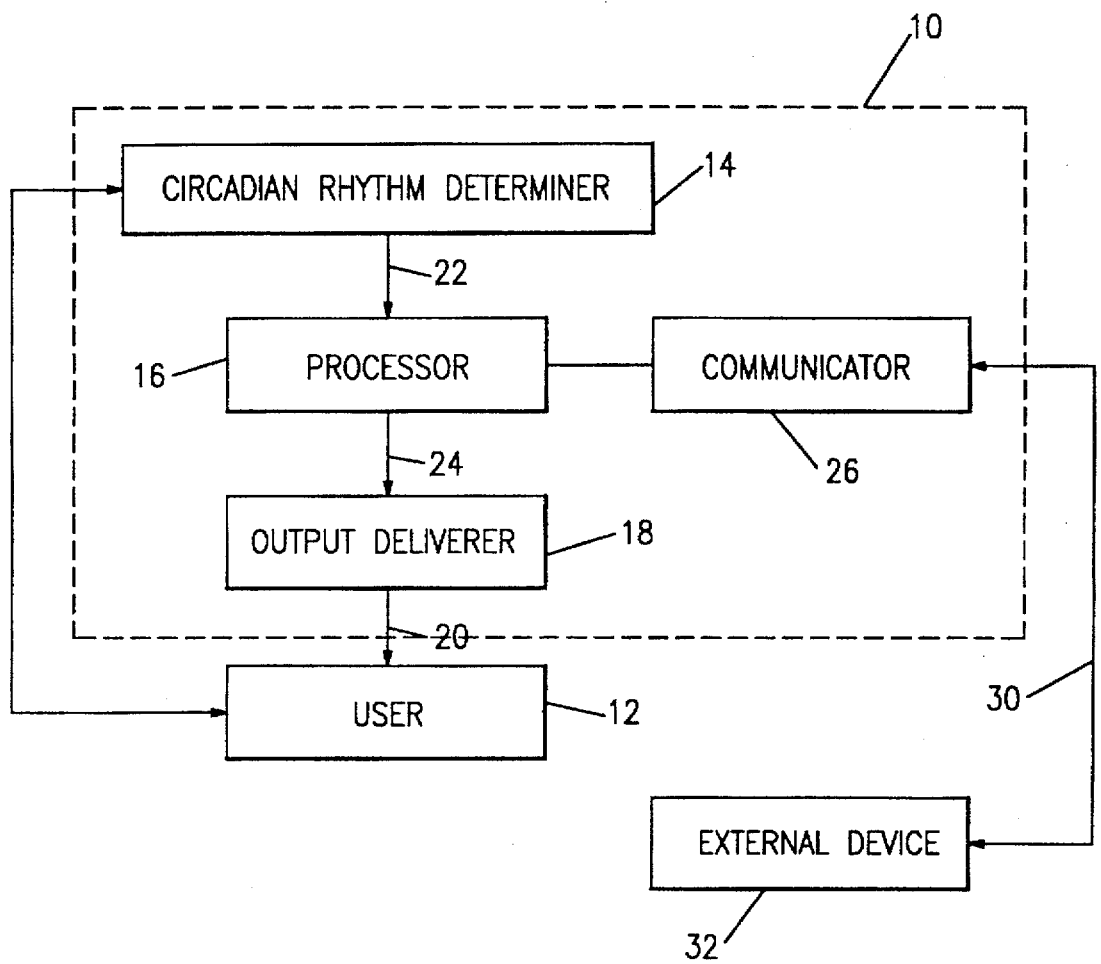
FIG. 1 is a block diagram illustrating components of an implantable pacemaker according to the present invention, and their relation to a patient and an external device.

Referring now to FIG. 1, there is shown a block diagram illustrating a pacemaker 10 according to the present invention in relation to a patient 12. As can be seen, the pacemaker 10 comprises a circadian rhythm detector 14, a processor 16 and output circuitry 18. The processor 16 is coupled to the circadian rhythm detector 14 by a coupler 20, and is coupled to the output circuitry 18 by a coupler 22.

The output circuitry 18 delivers pacing pulses 24 to the patient 12. The circadian rhythm detector 14 determines the beginning and ending of the patient's sleep cycle through a sensor 26. Upon determining that the patient has begun or has ended a period of sleep, the circadian rhythm detector 14 transmits the determination to the processor 16 through coupler 20. The processor 16 receives the determinations transmitted from the circadian rhythm detector 14 indicating the beginning or ending of the patient's sleep cycle, and in response, transitions the value of at least one parameter to another value. The processor 16 transmits the second value of the parameter to the output circuitry 18 which alters the pacing pulses sent to the patient.

One or more of following parameters can define the pacing pulses 24: pacing mode, base rate, maximum tracking rate, atrial refractory period, ventricular refractory period, 2:1 block rate, blanking period, atrial sensitivity, ventricular sensitivity, atrial tachycardia detect rate, tachycardia rate limit (such as disclosed in U.S. Pat. No. 4,944,928, incorporated herein by reference in its entirety), AV delay, AV/PV difference, atrial pacing pulses amplitude, ventricular pacing pulses amplitude, atrial pacing pulses pulse width, ventricular pacing pulses pulse width, hysteresis rate, slope, reaction time, recovery time, transfer curve, PMT detection and response criteria, sensor transfer curves, fast response, VARIO, histogram and event record recording parameters, PVC detection criteria, PVC response criteria and certain pacing pulses configurations (such as bipolar tip to ring, unipolar tip to case, unipolar ring to case, or with more than one lead, tip to tip or tip to ring), as well as corresponding sensing configurations. Other parameters could also be used as will be understood by those with skill in the art with reference to the disclosure herein.

The circadian rhythm detector 14 can comprise a real time clock, an activity detector, or other appropriate instruments as will be understood by those with skill in the art with reference to the disclosure herein. Any method of detecting circadian rhythms (or cycles) in a patient could be incorporated into the present invention. For example, U.S. Pat. No. 5,476,483 to Bornzin et al., incorporated herein by reference in its entirety, discloses a suitable activity detector. Other U.S. Pat. Nos. 4,922,930 to Adkins et al.; 5,143,065 to Adkins et al.; and 5,300,092 to Schaldach, each incorporated herein by reference in its entirety, also disclose suitable circadian rhythm detectors.

In one embodiment of the present invention, the pacing pulses 24 are defined by at least two parameters, such as the parameters listed above. In response to detecting a first stage of a patient's circadian rhythm such as the beginning of a period of sleep by the circadian rhythm detector 14, the processor 16 begins to transition a first value of a first parameter to a second value of the first parameter by a first transfer curve. Additionally, the processor 16 begins to transition a first value of the second parameter to a second value of the second parameter by a second transfer curve. The processor 16 then regularly transmits new values of the first and second parameters to the output circuitry 18 utilizing the selected transfer curves to determine the intermediate values until the second value of the first parameter and the second value of the second parameter are reached. In response to these transmissions from the processor 16, the output circuitry 18 is capable of changing the pacing pulses 24 delivered to the patient 12 as required to produce pacing pulses appropriate for the stage of the circadian rhythm.

Further, the circadian rhythm detector 14 of the pacemaker 10 can additionally detect a start of a second stage of the patient's circadian rhythm, such as the start of a period of waking. In response to the start of this second stage, the processor 16 begins to transition the second value of the first parameter to a third value of the first parameter by a third transfer curve. Additionally, the processor 16 begins to transition the second value of the second parameter to a third value of the second parameter by a fourth transfer curve. The processor 16 then regularly transmits new values of the first and second parameters to the output circuitry 18 utilizing the selected transfer curves to determine the intermediate values until the third value of the first parameter and the third value of the second parameter are reached.

It should be noted that the value of a parameter during a period of waking or a period of sleep can be the same as the value of the same parameter during each subsequent period of waking or sleep. That is, the value of a parameter can cycle diurnally. In this example the third values of the first and second parameters could be identical to their respective first values, thus providing a method of transitioning two parameters between two different sets of values, with one set of curves for each transition direction.

Any of the transfer curves utilized by the processor 16 can be selected from the group consisting of a single step transition, a multi-step transition, a gradual linear transition, a gradual nonlinear transition and a combination of any of the foregoing. Further, the transfer curve used to transition one value of a parameter to a second value can be substantially identical or can be substantially nonidentical to the transfer curve used to transition one value of a different parameter to a second value.

Referring now to FIGS. 2A through 2K, there are depicted graphical representations of some of the various transfer curves that can be used to transition a parameter from one value to another value according to the present invention. In each of these graphical representations, the abscissa represents relative time and the ordinate represents relative value. "$T_1$" indicates the start of a stage of a patient's circadian rhythm, such as the beginning of a sleep cycle. "i" represents an initial value of a parameter at the start of the stage and "ii" represents the value of the parameter after being transitioned by the processor.

Figures 2A, 2B, 2C:
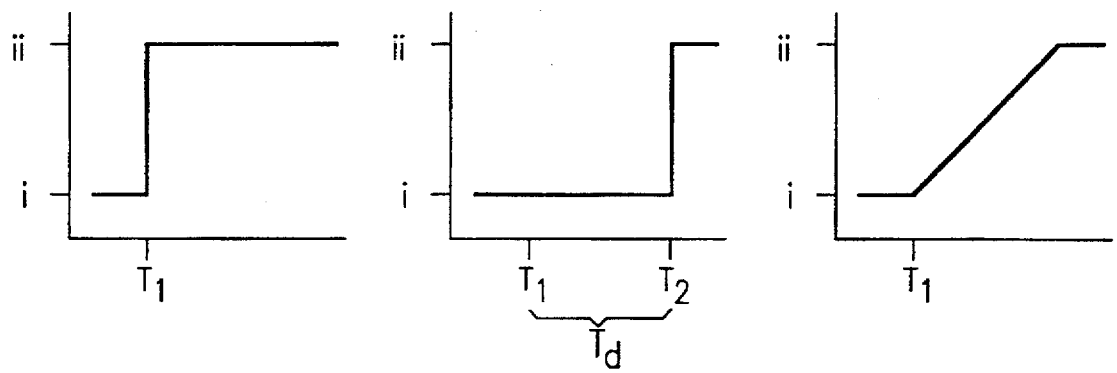
FIGS. 2A through 2K are graphical representations of some of the various transfer curves that can be used to transition a parameter from one value to another value according to the present invention.
Figure 2D:
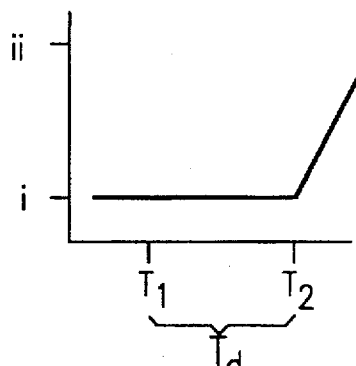

As can be appreciated by FIGS. 2A through 2K, a variety of transfer curves for transitioning the parameter from one value to another value are contemplated by the present invention. FIG. 2A shows a transfer curve consisting of a single step transition in the value of a parameter which occurs abruptly at the start of the stage. FIG. 2B depicts a transfer curve consisting of a single step transition from one value of the parameter to another value of the parameter. However, the transition begins a discreet time, shown as "$T_2$", after the beginning of the stage. The length of time between $T_1$ and $T_2$ is, therefore, a delay period "$T_d$" in the onset of transitioning the parameter from its value i to its value ii with respect to the beginning of the stage. FIG. 2C shows a transfer curve consisting of a gradual linear transition from value i of the parameter to value ii of the parameter. As can be seen, the transitioning begins coincidentally with the beginning of the stage at $T_1$. Similarly, FIG. 2D depicts a gradual linear transition in the value of the parameter from i to ii. However, as in FIG. 2B, the transfer curve of transitioning depicted in FIG. 2D also comprises a delay period "$T_d$".

Figure 2E:
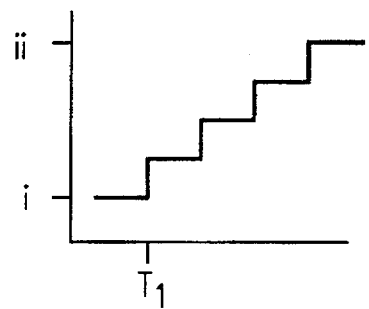
Figure 2F:
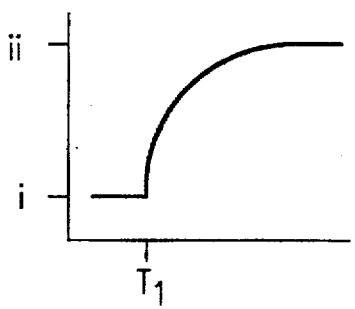
Figure 2G:
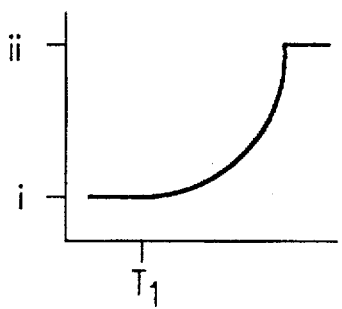
Figure 2H:
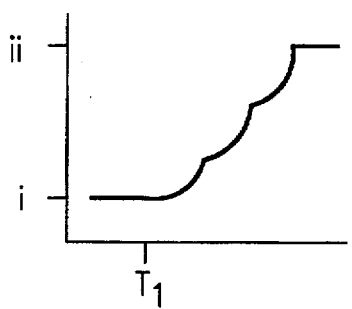
Figure 2I:
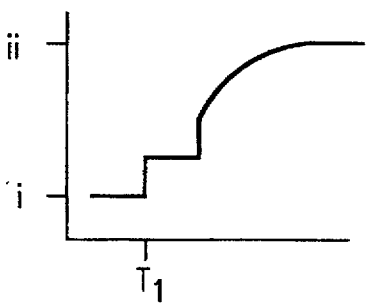
Figure 2J:
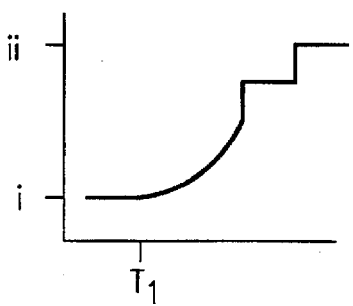
Figure 2K:
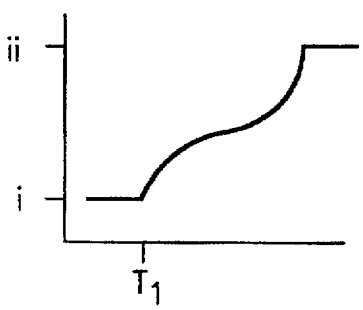

FIG. 2E depicts a transfer curve which consists of a series of single steps, where each step occurs abruptly. FIGS. 2F and 2G depict transfer curves that consist of gradual nonlinear transitioning. FIG. 2H depicts a transfer curve consisting of a series of steps where each step is a gradual nonlinear transition to an intervening value. FIGS. 2I, 2J and 2K depict transfer curves consisting of combinations of single step transitions, multi-step transitions, gradual linear transitions and gradual nonlinear transitions.

While FIGS. 2A through 2K depict some of the transfer curves contemplated by the present invention, other transfer curves can also be used as will be understood by those with skill in the art with reference to the disclosure herein. Additionally, any transfer curve used by the present invention can incorporate a delay period in which a change in the value of the parameter does not occur until a discreet time after the beginning of the stage of the circadian rhythm.

The pacemaker 10 can also include a telemetry means 28 coupled to the processor 16 by a telemetry channel 30 from an external device 32. The telemetry channel 30 can be an acoustic coupling, a magnetic channel, a radio frequency channel, or any other method of transmitting data from the external device 32 to the telemetry means 28. The processor 16 alters its internal settings based upon data received from the external device 32 via the telemetry channel 30 and the telemetry means 28. Thus, as is well known in the art, a physician or any other user operating the external device 32 could select the parameters to be transitioned, their transition values, their transition curves, and any delays associated with those transition curves. In addition, the physician or other user could also use this same technique to alter any programmable setting of the pacemaker 10 as is well known in the art.

In another embodiment of the present invention, the pacemaker 10 will alter the pacing pulses delivered to the patient according to a selectable transfer curve when the patient begins a period of sleep or waking. In this embodiment, the pacing pulses 24 are defined by at least one parameter. In response to the onset of a period of sleep or waking detected by the circadian rhythm detector 14, the processor 16 transitions a first value of the parameter to a second value of the parameter by a selectable transfer curve. The processor 16 then transmits to the output circuitry 18 the second value of the parameter and any intervening values of the parameter between the first value and the second value produced during transitioning. In responses, the output circuitry 18 is capable of changing the pacing pulses 24 delivered to the patient 12 as appropriate for the stage of the patient's circadian rhythm.

The processor 16 can set the selectable transfer curve to one of a plurality of transfer curves. Examples of transfer curves include a single step transition, a multi-step transition, a gradual linear transition, a gradual nonlinear transition and a combination of any of the foregoing.

This embodiment can also include a telemetry means 28 for receiving telemetry channel 30 from an external device 32. The processor 16 alters its internal settings based upon data received from the external device 32 via the telemetry channel 30 and the telemetry means 28. Thus, as is well known in the art, a physician or any other user operating the external device 32 could select the parameters to be transitioned, their transition values, their transition curves, and any delays associated with those transition curves. In addition, the physician or other user could also use this same technique to alter any programmable setting of the pacemaker 10 as is well known in the art.

In yet another embodiment of the present invention, any of the prior embodiments can be provided with a means to select a transition duration. The selected transition duration could be used by the processor 16 to determine the rate at which the intervening values of the selected parameters are transmitted to the output circuitry 18. Alternatively, the selected transition duration could be used by the processor 16 to determine both the rate that intervening values of the selected parameters are transmitted to the output circuitry 18 and the number of those intervening values. For example, at short transition durations, only a few intervening values may be transmitted, while at longer transition durations, additional intervening values would be transmitted.

While the present invention has been described with reference to an implantable cardiac pacemaker, the principles of the invention herein can also be applied to other implantable devices such cochlear implants, drug pumps, nerve and other tissue stimulators, cardiac defibrillators and mechanical heart assist devices. In a defibrillator according to the present invention, for example, the first parameter or the second parameter can be tachycardia zone limits. In a drug pump according to the present invention, the first parameter or the second parameter can be selected from the group consisting of frequency of drug delivery, dose of drug delivery and relative amounts of one or more drugs when delivering multiple drugs simultaneously or sequentially. In a cochlear implant, for example, the first parameter or the second parameter can be the filter setting.

Although the present invention has been discussed in considerable detail with reference to certain preferred embodiments thereof, other embodiments are possible. For example, though described in terms of detecting the beginning of period of sleep or waking, the circadian rhythm detector can determine the beginning, ending or other stages of the patient's circadian rhythm, and the present invention contemplates corresponding processes for these stages. Therefore, the spirit and scope of the appended claims should not be limited to the description of the preferred embodiments contained herein.

What is claimed is:

1. A rate-responsive pacemaker for delivering pacing pulses to a patient, the pacing pulses defined by a plurality of parameters including a first parameter and a second parameter, the plurality of parameters characterizing the rate, strength, form or similar attribute of the pulses, the pacemaker allowing for transitioning of at least two of the parameters in response to an onset of a stage in the patient's circadian rhythm, the pacemaker comprising:

pulse generating means for delivering the pacing pulses to the patient;

determining means for determining the onset of the stage in the patient's circadian rhythm and for transmitting the determination; and processing means, coupled to the determining means and coupled to the pulse generating means, for receiving the determination transmitted from the determining means and, in response, for transitioning a first value of the first parameter to a second value of the first parameter by a first transfer curve and for transitioning a first value of the second parameter to a second value of the second parameter by a second transfer curve, and for transmitting to the pulse generating means the second value of the first parameter, the second value of the second parameter and any intervening values of the first parameter and the second parameter produced during transitioning by the processing means; and wherein the pulse generating means can respond to the transmission from the processing means by changing the pacing pulses delivered to the patient.

2. The pacemaker of claim 1, wherein the stage determined by the determining means is a period of sleep by the patient.

3. The pacemaker of claim 1, wherein the stage determined by the determining means is a period of waking by the patient.

4. The pacemaker of claim 1, wherein the determining means includes a real time clock.

5. The pacemaker of claim 1, wherein the determining means includes an activity detector.

6. The pacemaker of claim 1, wherein the first parameter is selected from the group consisting of base rate, maximum tracking rate, atrial refractory period, ventricular refractory period, block rate, blanking period, atrial sensitivity, ventricular sensitivity, atrial tachycardia detect rate, tachycardia rate limit, AV delay, AV/PV difference, atrial output amplitude, ventricular output amplitude, atrial output pulse width, ventricular output pulse width, hysteresis rate, slope, reaction time, recovery time, transfer curve, PMT detection and response criteria, sensor transfer curves, fast response, VARIO, histogram and event record recording parameters, PVC detection criteria, and PVC response criteria.

7. The pacemaker of claim 1, wherein the second parameter is selected from the group consisting of base rate, maximum tracking rate, atrial refractory period, ventricular refractory period, block rate, blanking period, atrial sensitivity, ventricular sensitivity, atrial tachycardia detect rate, tachycardia rate limit, AV delay, AV/PV difference, atrial output amplitude, ventricular output amplitude, atrial output pulse width, ventricular output pulse width, hysteresis rate, slope, reaction time, recovery time, transfer curve, PMT detection and response criteria, sensor transfer curves, fast response, VARIO, histogram and event record recording parameters, PVC detection criteria, and PVC response criteria.

8. The pacemaker of claim 1, wherein the first transfer curve is selected from the group consisting of a single step transition, a multi-step transition, a gradual linear transition, a gradual nonlinear transition and a combination of any of the foregoing.

9. The pacemaker of claim 1, wherein the second transfer curve is selected from the group consisting of a single step transition, a multi-step transition, a gradual linear transition, a gradual nonlinear transition and a combination of any of the foregoing.

10. The pacemaker of claim 1, wherein the first transfer curve and the second transfer curve are substantially identical.

11. The pacemaker of claim 1, wherein the first transfer curve and the second transfer curve are substantially non-identical.

12. The pacemaker of claim 1, further including telemetry means coupled to the processing means for receiving input from an external device;
wherein the input instructs the processing means to change the first transfer curve to a different transfer curve.

13. The pacemaker of claim 1, further including telemetry means coupled to the processor for receiving input from an external device;
wherein the input instructs the processing means to change the second transfer curve to a different transfer curve.

14. The pacemaker of claim 1, further including telemetry means coupled to the processor for receiving input from an external device;
wherein the processor modifies at least one of the first value of the first parameter, the second value of the first parameter, the first value of the second parameter, or the second value of the second parameter in response to the received input.

15. A rate-responsive pacemaker for delivering pacing pulses to a patient, the pacing pulses defined by at least one parameter characterizing the rate, strength, form or similar attribute of the pulses, the pacemaker allowing for selective transitioning of the parameter from a first value to a second value in response to an onset of a stage in the patient's circadian rhythm, the pacemaker comprising:
pulse generating means for delivering the pacing pulses to the patient;
determining means for determining an onset of a stage in the patient's circadian rhythm and for transmitting the determination; and
processing means, coupled to the determining means and coupled to the pulse generating means, for receiving the determination transmitted from the determining means and, in response, for transitioning the first value of the parameter to a second value of the parameter by a selectable transfer curve, and for transmitting to the pulse generating means the second value of the first parameter and any intervening values of the parameter produced during transitioning by the processing means; and
wherein the processing means can set the selectable transfer curve to either a first transfer curve or a second transfer curve; and
wherein the pulse generating means can respond to the transmission from the processing means by changing the pacing pulses delivered to the patient.

16. The pacemaker of claim 15, wherein the stage determined by the determining means is a period of sleep by the patient.

17. The pacemaker of claim 15, wherein the stage determined by the determining means is a period of waking by the patient.

18. The pacemaker of claim 15, wherein the determining means includes a real time clock.

19. The pacemaker of claim 15, wherein the determining means includes an activity detector.

20. The pacemaker of claim 15, wherein the parameter is selected from the group consisting of base rate, maximum tracking rate, atrial refractory period, ventricular refractory period, block rate, blanking period, atrial sensitivity, ventricular sensitivity, atrial tachycardia detect rate, tachycardia rate limit, AV delay, AV/PV difference, atrial output amplitude, ventricular output amplitude, atrial output pulse width, ventricular output pulse width, hysteresis rate, slope, reaction time, recovery time, transfer curve, PMT detection and response criteria, sensor transfer curves, fast response, vario, histogram and event record recording parameters, PVC detection criteria, and PVC response criteria.

21. The pacemaker of claim 15, wherein the first transfer curve is selected from the group consisting of a single step transition, a multi-step transition, a gradual linear transition, a gradual nonlinear transition and a combination of any of the foregoing.

22. The pacemaker of claim 15, wherein the second transfer curve is selected from the group consisting of a single step transition, a multi-step transition, a gradual linear transition, a gradual nonlinear transition and a combination of any of the foregoing.

23. The pacemaker of claim 15, further including telemetry means coupled to the processing means for receiving input from an external device;
wherein the input instructs the processing means to change the first transfer curve to the second transfer curve.

24. An implantable medical device for delivering an output to a patient, the output defined by a plurality of parameters including a first parameter and a second parameter, the plurality of parameters characterizing the rate, strength, form or similar attribute of the output, the implantable medical device allowing for transitioning of at least two of the parameters in response to an onset of a stage in the patient's circadian rhythm, the implantable medical device comprising:
output generating means for delivering the output to the patient;
determining means for determining the onset of the stage in the patient's circadian rhythm and for transmitting the determination; and processing means, coupled to the determining means and coupled to the output generating means, for receiving the determination transmitted from the determining means and, in response, for transitioning a first value of the first parameter to a second value of the first parameter by a first transfer curve and for transitioning a first value of the second parameter to a second value of the second parameter by a second transfer curve, and for transmitting to the output generating means the second value of the first parameter, the second value of the second parameter and any intervening values of the first parameter and the second parameter produced during transitioning by the processing means; and wherein the output generating means can respond to the transmission from the processing means by changing the output delivered to the patient.

25. The implantable medical device of claim 24, wherein the stage determined by the determining means is a period of sleep by the patient.

26. The implantable medical device of claim 24, wherein the stage determined by the determining means is a period of waking by the patient.

27. The implantable medical device of claim 24, wherein the determining means includes a real time clock.

28. The implantable medical device of claim 24, wherein the determining means includes an activity detector.

29. The implantable medical device of claim 24, wherein in response to the determination transmitted by the determining means, the processing means delays the transitioning of the first and second parameters by a delay time interval.

30. The implantable medical device of claim 29, further including telemetry means coupled to the processing means for receiving input from an external device;

wherein the input instructs the processing means to select the delay time interval.

31. The implantable medical device of claim 24, wherein the first transfer curve is selected from the group consisting of a single step transition, a multi-step transition, a gradual linear transitions, a gradual nonlinear transition and a combination of any of the foregoing.

32. The implantable medical device of claim 24, wherein the second transfer curve is selected from the group consisting of a single step transition, a multi-step transition, a gradual linear transition, a gradual nonlinear transition and a combination of any of the foregoing.

33. The implantable medical device of claim 24, wherein the first transfer curve and the second transfer curve are substantially identical.

34. The implantable medical device of claim 24, wherein the first transfer curve and the second transfer curve are substantially nonidentical.

35. The implantable medical device of claim 24, further including telemetry means coupled to the processing means for receiving input from an external device;

wherein the input instructs the processing means to change the first transfer curve to a different transfer curve.

36. The implantable medical device of claim 24, further including telemetry means coupled to the processor for receiving input from an external device;

wherein the input instructs the processing means to change the second transfer curve to a different transfer curve.

37. The implantable medical device of claim 24, wherein at least part of the output is selected from the group consisting of tissue stimulating pulses, an aliquot of a pharmaceutical agent, and an application of mechanical force.

38. An implantable medical device for delivering an output to a patient, the output defined by at least one parameter characterizing the rate, strength, form or similar attribute of the output, the implantable medical device allowing for selective transitioning of the parameter from a first value to a second value in response to an onset of a stage in the patient's circadian rhythm, the implantable medical device comprising:

output generating means for delivering the output to the patient;

determining means for determining an onset of a stage in the patient's circadian rhythm and for transmitting the determination; and processing means, coupled to the determining means and coupled to the output generating means, for receiving the determination transmitted from the determining means and, in response, for transitioning the first value of the parameter to a second value of the parameter by a selectable transfer curve, and for transmitting to the output generating means the second value of the first parameter and any intervening values of the parameter produced during transitioning by the processing means; and wherein the processing means can set the selectable transfer curve to either a first transfer curve or a second transfer curve; and wherein the output generating means can respond to the transmission from the processing means by changing the output delivered to the patient.

39. The implantable medical device of claim 38, wherein the stage determined by the determining means is a period of sleep by the patient.

40. The implantable medical device of claim 38, wherein the stage determined by the determining means is a period of waking by the patient.

41. The implantable medical device of claim 38, wherein the determining means includes a real time clock.

42. The implantable medical device of claim 38, wherein the determining means includes an activity detector.

43. The implantable medical device of claim 38, wherein the parameter is selected from the group consisting of base rate, maximum tracking rate, atrial refractory period, ventricular refractory period, block rate, blanking period, atrial sensitivity, ventricular sensitivity, atrial tachycardia detect rate, tachycardia rate limit, AV delay, AV/PV difference, atrial output amplitude, ventricular output amplitude, atrial output pulse width, ventricular output pulse width, hysteresis rate, slope, reaction time, recovery time, transfer curve, PMT detection and response criteria, sensor transfer curves, fast response, vario, histogram and event record recording parameters, PVC detection criteria, and PVC response criteria.

44. The implantable medical device of claim 38, wherein the first transfer curve is selected from the group consisting of a single step transition, a multi-step transition, a gradual linear transition, a gradual nonlinear transition and a combination of any of the foregoing.

45. The implantable medical device of claim 38, wherein the second transfer curve is selected from the group consisting of a single step transition, a multi-step transition, a gradual linear transition, a gradual nonlinear transition and a combination of any of the foregoing.

46. The implantable medical device of claim 38, further including telemetry means coupled to the processing means for receiving input from an external device;

wherein the input instructs the processing means to change the first transfer curve to the second transfer curve.

47. The implantable medical device of claim 38, wherein at least part of the output is selected from the group consisting of an aliquot of a pharmaceutical agent, an application of mechanical force and an application of electrical stimulation.

48. The implantable medical device of claim 38, wherein the processing means in response to the determination received from the determining means delays the transition of the parameter by a delay time interval.

49. The implantable medical device of claim 48, further including telemetry means coupled to the processing means for receiving input from an external device;

wherein the input instructs the processing means to select the delay time interval.

* * * * *